United States Patent [19]
Taverne et al.

[11] Patent Number: 5,225,409
[45] Date of Patent: Jul. 6, 1993

[54] BENZOXAZINONE COMPOUNDS

[75] Inventors: Thierry Taverne, St. Martins, les Boulogne; Isabelle Lesieur, Gondecourt; Patrick Depreux, Armentieres; Daniel H. Caignard, Paris; Béatrice Guardiola, Neuilly sur Seine; Gérard Adam, Le Mesnil le Roi; Pierre Renard, Versailles, all of France

[73] Assignee: Adir et Compagnie, Courbevoie, France

[21] Appl. No.: 766,664

[22] Filed: Sep. 26, 1991

[30] Foreign Application Priority Data

Sep. 26, 1990 [FR] France .................. 90 11866

[51] Int. Cl.$^5$ ............... C07D 265/36; C07D 113/02; A61K 31/535
[52] U.S. Cl. .................... 514/230.5; 514/105
[58] Field of Search ............. 544/105; 514/230.05

[56] References Cited

U.S. PATENT DOCUMENTS 3,770,734 11/1973 Pesson ................... 544/105

OTHER PUBLICATIONS

Goodman & Gilman's "The Pharmacological Basis of Therapeutics", 8th Edition, 1990 (Pergamon Press), p. 44.

Journal of Pharmacological Methods, 13, 193–200, (1985), 193–200, Martin.

Primary Examiner—Raymond J. Shah
Assistant Examiner—Philip I. Datlow
Attorney, Agent, or Firm—Gordon W. Hueschen

[57] ABSTRACT

Benzoxazinone compounds of general formula (I):

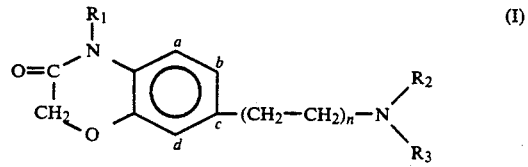

useful in the treatment of serotoninergic disorders, especially anxiety and schizophrenia, requiring for their treatment compounds which are 5-HT$_{1A}$ receptor agonists, wherein $R_1$, $R_2$, $R_3$, and n are as defined in the description, and medicinal products containing the same, are disclosed.

13 Claims, No Drawings

BENZOXAZINONE COMPOUNDS

The present invention relates to new benzoxazinone compounds, to a process for preparing these and to pharmaceutical compositions containing them.

Some benzoxazinone compounds were disclosed in U.S. Pat. No. 3,770,734. These compounds could be use in central nervous system diseases. In comparison with these previous compounds, the compounds of the present invention are characterized by their more potent activity. So that we can prove unambiguously their better activity, our compounds were compared to the previous ones using the same tests as reported in the pharmacological study of this application. Our compounds show an unpredictable better activity. Moreover we used new tests showing the mechanism of their activity, which could not be known when the U.S. Pat. No. 3,770,734 was filed.

Actually, the very high affinity and selectivity of the compounds of the invention for serotoninergic receptors $5HT_1A$ renders them usable in the treatment of diseases of the serotoninergic system, and more especially depression, stress, anxiety and schizophrenia, at lower doses than the compounds of the prior art. This feature, combined with their low toxicity, renders the compounds of the invention usable with much greater safety than the compounds of the prior art, which is especially advantageous in view of the frailty of the populations at which this type of treatment is aimed.

In addition, some compounds of the invention possess good analgesic, hypnotic or antihypertensive properties, or may be used in the prevention of atheroma.

More specifically, the present invention relates to the compounds of general formula (I):

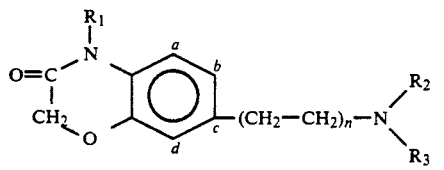

in which:
$R_1$ represents a hydrogen atom or a lower alkyl group,
n represents 1 or 2,
$R_2$ and $R_3$, which may be identical or different, each represents, independently of one another:
  a hydrogen atom or a lower alkyl or phenyl(lower alkyl) or phenyl group, or hydroxy phenyl hydroxy lower alkyl group or $R_2$ and $R_3$, together with the nitrogen atom which carries them, form a mono- or bicyclic heterocyclic system, each ring being five- or six-membered and optionally including in its carbon skeleton one or two hetero atoms selected from nitrogen, oxygen and sulfur, where appropriate substituted or otherwise on the possible nitrogen atom(s) with one or more lower alkyl, phenyl, phenyl(lower alkyl), pyridyl or pyrimidinyl groups, or phenyl groups substituted with one or more lower alkyl, trifluoromethyl or lower alkoxy groups or halogen atoms, or phenyl(lower alkyl) groups substituted on the phenyl ring with one or more lower alkyl, trifluoromethyl or lower alkoxy groups or halogen atoms, or pyridyl groups substituted with one or more lower alkyl, trifluoromethyl or lower alkoxy groups or halogen atoms, their enantiomers, diastereoisomers and epimers as well as their addition salts with a pharmaceutically acceptable acid or a pharmaceutically acceptable base when $R_1 = H$.

Among pharmaceutically acceptable acids, hydrochloric, sulfuric, tartaric, maleic, fumaric, oxalic, methanesulfonic, camphoric, ethanesulfonic and citric acid, and the like, may be mentioned without implied limitation. Among pharmaceutically acceptable bases, sodium, potassium and calcium hydroxides, as well as sodium, potassium and calcium carbonates, and the like, may be mentioned without implied limitation.

The invention also encompasses the process for preparing the compounds of general formula (I), wherein a derivative of formula (II):

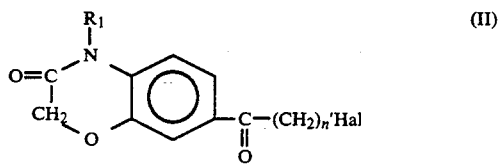

with Hal representing a halogen atom and $R_1$, A and X having the same definition as in the formula (I), and n' represents 1 or 3, is used as a starting material, which compound is treated with a trialkylsilane in an acid medium to yield a compound of formula (III):

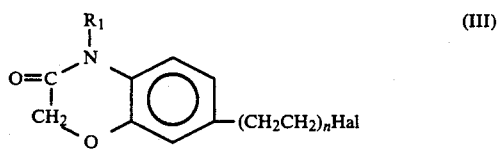

with A, X, $R_1$, n and Hal as defined above, which is condensed:
either with an amine of formula:

with $R_2$ and $R_3$ having the same definition as above, to yield a compound of formula (I):

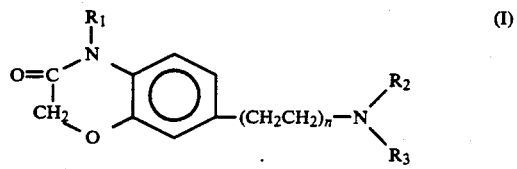

with $R_1$, n, $R_2$ and $R_3$ having the same definition as above, the isomers of which are separated, where appropriate, and purified if necessary by chromatography or crystallization, The compounds of formula (I) possess advantageous pharmacological properties.

Binding tests showed that the compounds of the invention behave as very potent ligands of $5\text{-HT}_{1A}$ receptors. This affinity is accompanied by a very great selectivity with respect to other receptors, in particular D2 and α2, in contrast to the behavior observed with the compounds of the prior art.

The compounds of the invention are of low toxicity, and possess good activity in the pigeon conflict test, confirming the activity detected by binding. Some of them possess, moreover, an excellent analgesic activity, others a noteworthy hypnotic, antihypertensive or normolipemic activity.

The compounds of the invention hence find their application in the treatment of distress, anxiety, depression, schizophrenia, psychoses, dementia, senile dementia, aggressiveness and agitation, but also, for some of the compounds and sleep disorders.

The subject of the present invention is also pharmaceutical compositions containing as active principle at least one compound of general formula (I) or one of its addition salts with a pharmaceutically acceptable acid or, where appropriate, with a pharmaceutically acceptable base, alone or in combination with one or more non-toxic, inert excipients or vehicles.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The dosage varies according to the patient's age and weight and the nature and severity of the condition, as well as the administration route. The latter may be oral, nasal, rectal or parenteral.

Generally speaking, single doses range between 0.05 and 30 mg for conditions affecting mental behavior and between 1 mg and 500 mg for the treatment of pain and of arterial hypertension, that is to say, taken in one to three doses per 24 hours.

The examples which follow illustrate the invention and in no way limit the latter.

The 1H nuclear magnetic resonance spectra were recorded using TMS (tetramethylsilane) as an internal reference. The chemical shifts are expressed in parts per million (ppm). The infrared spectra were run in the form of a potassium bromide disk containing approximately 1% of the product to be analyzed.

The preparations do not form part of the invention, but are useful for carrying out the synthesis of the compounds of the invention.

PREPARATION 1

7-(BROMOACETYL)2,3-DIHYDRO-3-OXO 1,4-BENZOXAZINE 0.01 mol of 7-acetylbenzoxazinone, described in Application EP 223,674, is dissolved in 100 cm$^3$ of methylene chloride. 0.011 mol of bromine is added dropwise and with stirring via a dropping funnel, and stirring is maintained for 13 hours. The mixture is filtered and evaporated to dryness and the residue is recrystallized.

PREPARATION 2

7-(4-BROMOBUTYL)2,3-DIHYDRO 3-OXO 1,4-BENZOXAZINE

In a 500-cm$^3$ ground-necked flask surmounted by a condenser, and placed in an oil bath, 40.8 g (0.15 mol) of 7-(4-bromoBUTYRYL)2,3-dihydro 3-oxo 1,4-benzoxazine described in European Patent Application EP 0223674 are dissolved in 90 cm$^3$ of trifluoroacetic acid with magnetic stirring and while the temperature is stabilized at 60° C. 52.7 cm$^3$ (0.33 mol) of triethylsilane are introduced dropwise via a dropping funnel. After the addition, the heating is stopped and the mixture is then left stirring vigorously for 30 hours. The reaction medium is hydrolyzed by pouring it into ice-cold water, and the precipitate obtained is drained and washed with water until the filtrate is neutral and then with hexane. The product is dried and recrystallized in absolute ethanol. Yield: 80%

PREPARATION 3

4-METHYL-7-(2-BROMOETHYL)-3-OXO-2,3-DIHYDRO-1,4-BENZOXAZINE 0.01 mol of 4-methyl-7-acetyl-3-oxo-2,3-dihydro-1,4-benzoxazine, obtained in European Patent Application 0,223,674, is dissolved in methylene chloride, 0.012 mol of bromine is added with stirring via a dropping funnel. Stirring is maintained for two hours, and the reaction medium is then left in a oil bath at 40° C. with stirring for 2 hours. The mixture is filtered. The solvent is evaporated off. The residue is recrystallized.

The 4-methyl-7-(bromoacetyl)-3-oxo-2,3-dihydrobenzoxazine is converted to 4-methyl-7-(2-bromoethyl)-3-oxo-2,3-dihydro-1,4-benzoxazine by catalytic hydrogenation in an acetic acid medium in the presence of palladinized charcoal, or by the action of trialkylsilane in a trifluoroacetic acid medium.

PREPARATION 4

7-(4-BROMOBUTYL)-4-METHYL-2,3-DIHYDRO-3-OXO-1,4-BENZOXAZINE

Using the procedure described in Preparation 2, but replacing 7-(4-bromo butyry)2,3-dihydro-3-1,4-benzoxazine by 7-(4-bromobutyryl)-4-methyl-2,3-dihydro-3-oxobenzoxazine, described in Application EP 0,223,674, the produce of the title is obtained.

EXAMPLE 1

4-METHYL-7-(4-AMINOBUTYL)2,3-DIHYDRO 3-OXO 1,4-BENZOXAZINE (HYDROCHLORIDE)

In a 250 cm$^3$ ground-necked flask, 8.1 g (0.03 mol) of 4-methyl-6-(4-bromobutyl)2,3-dihydro-3-oxo-1,4-benzoxazine and 0.9 g of potassium iodide are dissolved in 120 cm$^3$ of methanol and 30 cm$^3$ of chloroform. A stream of gaseous ammonia is bubbled into the solution to the point of saturation, equivalent to approximately 2.6 g of ammonia, and a reflux condenser is then fitted. The temperature is stabilized at 50° C. with an oil bath and the mixture is left stirring magnetically for 72 hours. After cooling, the reaction mixture is evaporated on a water bath under vacuum. The residue is ground with distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized in absolute ethanol.

Infrared spectrometry:
3100–2800 cm$^{-1}$: $\nu$ (C—H)
2750–2400 cm$^{-1}$: $\nu$(NH+)
1600–1580 cm$^{-1}$: $\nu$ (C=C) aromatic The base is obtained by dissolution of the hydrochloride in water, alkalinization and three extractions with chloroform. The chloroform phases are combined, dried over calcium chloride and evaporated to dryness. The residue may be used without further purification as a starting material.

EXAMPLE 2

4-METHYL-7-[4-(N-METHYL-N-BENZYLAMINO)BUTYL]-2,3-DIHYDRO-3-OXO-1,4-BENZOXAZINE 0.04 mol of N-methyl-N-benzylamine and 0.02 mol of 4-methyl-7-(4-bromobutyl)-2,3-dihydro-3-oxo-1,4-benzoxazine, the latter being dissolved beforehand in 120 cm$^3$ of dioxane, are introduced into a 100-cm$^3$ ground-necked flask fitted with a reflux condenser. The mixture is heated to reflux for 96 hours with magnetic stirring. After cooling, the reaction mixture is filtered and the filtrate is then evaporated on a water bath under vacuum. The residue is taken up with 50 cm$^3$ and alkalinized with 10 cm$^3$ of normal sodium hydroxide solution.

The mixture is extracted three times with 60 cm$^3$ of chloroform. The organic solutions are combined, dried over calcium chloride, filtered and evaporated on a water bath under vacuum. The residue is taken up with petroleum ether, drained, dried and recrystallized.

EXAMPLE 3

4-METHYL-7-[4-(N-METHYLAMINO)BUTYL]-2,3-DIHYDRO-3-OXO-1,4-BENZOXAZINE (HYDROCHLORIDE)

Using the procedure described in Example 1, but replacing ammonia by N-methylamine, the product of the title is obtained.
Infrared:
3100–2600 cm$^{-1}$ : $\nu$ NH and $\nu$CH

EXAMPLE 4

4-METHYL-7-(4-ISOPROPYLAMINOBUTYL)-2,3-DIHYDRO-3-OXO-1,4-BENZOXAZINE (HYDROCHLORIDE)

0.2 mol of isopropylamine and 0.02 mol of 4-methyl-7-(4-bromoethyl)-2,3-dihydro-3-oxo-1,4-benzoxazine, the latter being dissolved beforehand in 120 cm$^3$ of dioxane, are introduced into a 250-cm$^3$ ground-necked flask equipped with a reflux condenser. The mixture is heated to reflux for 2 days with magnetic stirring. After cooling, the mixture is evaporated to dryness, the residue is alkalinized and extracted three times with chloroform, and the organic phases are combined, dried over calcium chloride and evaporated. The residue is taken up in diethyl ether, and 10 ml of anhydrous ether saturated with hydrochloric acid are added. The product is drained. It is recrystallized.
Infrared:
3100–2650 cm$^{-1}$ : $\nu$ NH and $\nu$ CH

EXAMPLE 5

4-METHYL-7-(4-PROPYLAMINOBUTYL)-2,3-DIHYDRO-3-OXO-1,4-BENZOXAZINE (HYDROCHLORIDE)

Using the procedure described in Example 4, but replacing isopropylamine by n-propylamine, the product of the title is obtained.
Spectral characteristics:
Infrared:
3100–2650 cm$^{-1}$ : $\nu$ NH and $\nu$ CH

EXAMPLE 6

(RS)-4-METHYL-7-[2-}2-(3-HYDROXYPHENYL)-2-HYDROXYETHYL]-AMINO}ETHYL]-2,3-DIHYDRO-3-OXO-1,4-BENZOXAZINE

In a 250 cm$^3$ ground-necked flask surmounted by a condenser, 4.2 g (0.022 mol) of norphenylephrine are dissolved in 120 cm$^3$ of ethanol and 5.5 cm$^3$ of triethylamine. The mixture is left stirring at room temperature for ¼ hour and 5.4 g (0.02 mol) of 4-methyl-7-(2-bromoethyl) 2,3-dihydro 3-oxo 1,4-benzoxazine and 0.3 g (0.002 mol) of potassium iodide are then introduced. The mixture is left stirring magnetically under reflux for 96 hours with a calcium chloride guard tube. The reaction medium is cooled to 5° C. and the precipitate is drained, dried and then recrystallized.
Infrared spectrometry:
3290 cm$^{-1}$ : $\nu$ (O—H)
3120–3320 cm$^{-1}$ : $\nu$ (N—H)
3100–2800 cm$^{-1}$ : $\nu$ (C—H)
2750–2400 cm$^{-1}$ : $\nu$ (NH+)
1600–1580 cm$^{-1}$ : $\nu$ (C=C) aromatic

EXAMPLE 7

4-METHYL-7-(2-DIPROPYLAMINOETHYL)-2,3-DIHYDRO-3-OXO-1,4-BENZOXAZINE (HYDROCHLORIDE)

5.4 g of 4-methyl-7-(2-bromoethyl)2,3-dihydro 3-oxo 1,4-benzoxazine, dissolved beforehand in 120 cm$^3$ of dioxane and 6 cm$^3$ of (0.044 mol) of dipropyl-amine, are introduced into a 250 cm$^3$ round-necked flask equipped with a reflux condendser. The mixture is heated to reflux with magnetic stirring for 4 days. After cooling, the reaction mixture is filtered and the filtrate is then evaporated on a water bath under vacuum. The residue is ground with distilled water and extracted with ethyl acetate. The organic phase is recovered and evaporated to dryness and the residue is taken up with 5% HCl solution. The acidic aqueous phase is washed with ethyl acetate and then alkalinized with 10% sodium hydroxide solution. It is extracted with ethyl acetate and the organic phase is washed with distilled water and then dried over potassium carbonate. The solvent is evaporated off on a water bath under vacuum. The residue is taken up in absolute ethanol, a stream of gaseous HCl is bubbled through and the mixture is then evaporated to dryness on a water bath under vacuum. The residue is ground in toluene or ether, then drained and dried. The product is recrystallized in anhydrous acetone.
Infrared spectrometry:
3050–2850 cm$^{-1}$ : $\nu$ (C—H)
2800–2300 cm$^{-1}$ : $\nu$ (NH+)
1600–1580 cm$^{-1}$ : $\nu$ (C=C) aromatic

EXAMPLE 8

4-METHYL-7-{2-[4-(2,3,4-TRIMETHOXYBENZYL)-1-(PIPERAZINYL]-ETHYL}2,3-DIHYDRO 3-OXO 1,4-BENZOXAZINE (DIHYDROCHLORIDE)

5.4 g (0.02 mol) of 4-methyl-7-(2-bromoethyl)2,3-dihydro 3-oxo 1,4-benzoxazine, dissolved beforehand in 150 cm$^3$ of dioxane, followed by 5.9 g (0.022 mol) of trimetazidine and 1 g of triethylamine (0.01 mol), are introduced into a 250-cm$^3$ ground-necked flask equipped with a reflux condenser. The mixture is heated to reflux with magnetic stirring for 96 hours. After cooling, the reaction mixture is drained and the filtrate is then evaporated on a water bath under vacuum. The residue is taken up with 5% HCl solution. The acidic aqueous phase is washed with ethyl acetate and then alkalinized with 10% sodium hydroxide solution. It is extracted with ether and the organic phase is washed with distilled water and then dried over calcium chloride. The organic phase is filtered and evaporated to dryness on a water bath under vacuum. The residue is taken up in absolute ethanol, a stream of gaseous HCl is bubbled through and the product is drained and then dried. It is recrystallized in methanol.

Infrared spectrometry:
3050–2800 cm$^{-1}$ : $\nu$ (C—H)
2700–2100 cm$^{-1}$ : $\nu$ (NH+)
1600–1580 cm$^{-1}$ : $\nu$ (C=C) aromatic

EXAMPLES 9 to 11

4-METHYL-7-[2-(4-ARYL-1-PIPERAZINYL)-ETHYL]-2,3-DIHYDRO-3-OXO-1,4-BENZOXAZINE 5.4 g of 4-methyl-7-(2-bromoethyl)2,3-dihydro-3-oxo 1,4-benzoxazine, dissolved beforehand in 150 cm$^3$ of dioxane and 0.022 mol of 4-arylpiperazine, are introduced into a 250-cm$^3$ ground-necked flask equipped with a reflux condenser. The mixture is heated to reflux with magnetic stirring for 96 hours.

The reaction mixture is evaporated on a water bath under vacuum and the residue is rinsed with 5% HCl solution and then with distilled water, drained and washed with ethyl acetate. The product is dried and recrystallized.

The purification is slightly different if the desired product is the basic form.

EXAMPLE 9

4-METHYL-7-{2-[4-(3-TRIFLUOROMETHYL-PHENYL)-1-PIPERAZINYL]ETHYL}2,3-DIHYDRO-3-OXO-1,4-BENZOXAZINE (MONOHYDROCHLORIDE)

Infrared spectrometry:
3100–2800 cm$^{-1}$ : $\nu$ (C—H)
2700–2300 cm$^{-1}$ : $\nu$ (NH+)
1600–1580 cm$^{-1}$ : $\nu$ (C=C) aromatic

EXAMPLE 10

4-METHYL-7-{2-[4-(2-METHOXYPHENYL)-1-PIPERAZINYL]ETHYL}2,3-DIHYDRO 3-OXO-1,4-BENZOXAZINE (MONOHYDROCHLORIDE)

Infrared spectrometry:
3000–2800 cm$^{-1}$ : $\nu$ (C—H)
2750–2400 cm$^{-1}$ : $\nu$ (NH+)
1600–1580 cm$^{-1}$ : $\nu$ (C=C) aromatic

EXAMPLE 11

4-METHYL-7-{2-[4-(4-FLUOROPHENYL)-1-PIPERAZINYL]ETHYL}-2,3-DIHYDRO-3-OXO-1,4-BENZOXAZINE (DIHYDROCHLORIDE)

Infrared spectrometry:
3100–2800 cm$^{-1}$ : $\nu$ (C—H)
2700–2100 cm$^{-1}$ : $\nu$ (NH+)
1600–1580 cm$^{-1}$ : $\nu$ (C=C) aromatic

EXAMPLE 12

7-{2-[4-(3-TRIFLUOROMETHYLPHENYL)-1-PIPERAZINYL]ETHYL}-2,3-DIHYDRO-3-OXO-1,4-BENZOXAZINE 5.2 g (0.02 mol) of 7-(2-bromoethyl)-2,3-dihydro-3-oxo-1,4-benzoxazine, dissolved beforehand in 150 cm$^3$ of dioxane, followed by 0.022 mol of 1-(3-trifluoromethyl phenyl)piperazine and 0.2 g of potassium iodide, are introduced into a 250-cm$^3$ ground-necked flask equipped with a reflux condenser. The mixture is heated to reflux with magnetic stirring for 96 hours.

The reaction mixture is evaporated on a water bath under vacuum and the precipitate is ground in 5% HCl solution, drained and washed with water. The precipitate is taken up in 10% aqueous Na$_2$CO$_3$ solution and extracted with ethyl acetate; the organic phase is washed with water and the solvent is then evaporated off. The residue is dissolved in a minimum amount of ethanol and a stream of gaseous hydrogen chloride is bubbled through; the precipitate is then drained. The precipitate is taken up in water containing 2 equivalents of K2CO3 and the mixture is stirred for 1 to 2 hours. The precipitate is drained and washed with distilled water. The product is dried and recrystallized in propanol.

Infrared spectrometry:
3160 cm$^{-1}$ : $\nu$ (N—H)
3100–2800 cm$^{-1}$ : $\nu$ (C—H) —CH$_2$—
1600–1580 cm$^{-1}$ : $\nu$ (C=C) aromatic

EXAMPLES 13 to 17

Using the procedure described in Examples 6 and 8 to 11, but replacing 4-methyl-7-(2-bromoethyl)2,3-dihydro 3-oxo 1,4-benzoxazine by 4-methyl-7-(4-bromobutyl)-2,3-dihydro-3-oxo-1,4-benzoxazine, the following are obtained:

EXAMPLE 13

4-METHYL-7-[4-{[2-(3-HYDROXYPHENYL)-2-HYDROXYETHYL]AMINO}BUTYL]-2,3-DIHYDRO-3-OXO-1,4-BENZOXAZINE

EXAMPLE 14

4-METHYL-7-{4-[4-(2,3,4-TRIMETHOXYBENZYL)-1-PIPERAZINYL]-BUTYL}-2,3-DIHYDRO-3-OXO-1,4-BENZOXAZINE DIHYDROCHLORIDE

EXAMPLE 15

4-METHYL-7-{4-[4-(3-TRIFLUOROMETHYL-PHENYL)-1-PIPERAZINYL]BUTYL}-2,3-DIHYDRO-3-OXO-1,4-BENZOXAZINE MONOHYDROCHLORIDE

Melting point : 205° C.

EXAMPLE 16

4-METHYL-7-{4-[4-(2-METHOXYPHENYL)-1-PIPERAZINYL]BUTYL}-2,3-DIHYDRO-3-OXO-1,4-BENZOXAZINE MONOHYDROCHLORIDE

EXAMPLE 17

4-METHYL-7-{4-[4-(4-FLUOROPHENYL)-1-PIPERAZINYL]BUTYL}-2,3-DIHYDRO-3-OXO-1,4-BENZOXAZINE BASE

Melting point : 89°–90° C.

EXAMPLE 18

7-(2-AMINOETHYL)-3-OXO-2,3-DIHYDRO-1,4-BENZOXAZINE

In a 250-cm³ ground-necked flask, 0.01 mol of 7-(2-bromoethyl)-3-oxo-2,3-dihydro-1,4-benzoxazine and 0.3 g of potassium iodide are dissolved in 30 cm³ of dimethylformamide.

A stream of gaseous ammonia is bubbled into the solution to the point of saturation and a reflux condenser is fitted. The temperature is stabilized at 50° C. with an oil bath and the mixture is then left stirring magnetically for 72 hours. After cooling, the reaction mixture is evaporated on a water bath under vacuum. The residue is ground in distilled water acidified with 5% HCl solution, and then drained. The filtrate is recovered, washed with ethyl acetate and then alkalinized with 10% sodium hydroxide solution. It is extracted with chloroform, leaving the 2 phases agitating for ½ hour, and the organic phase is washed with distilled water and then dried over calcium chloride. The organic phase is evaporated on a water bath under vacuum, the residue is then taken up in absolute ethanol, a stream of gaseous HCl is bubbled through and the mixture is then evaporated to dryness on a water bath under vacuum. The product is dried and then recrystallized.

EXAMPLE 19

4-METHYL-7-(2-PROPYLAMINOETHYL)-3-OXO-2,3-DIHYDRO-1,4-BENZOXAZINE

Using the procedure described in Preparation 9, but replacing 6-(2-bromoethyl)-3-oxo-2,3-dihydro-1,4-benzoxazine by 4-methyl-7-(2-bromoethyl)-3-oxo-2,3-dihydro-1,4-benzoxazine, the product of the title is obtained.

Using the procedure described in previous Examples, the following are obtained:

7-{2-[4-(2-METHOXY PHENYL)PIPERAZIN-1-YL]ETHYL}-2,3-DIHYDRO-3-OXO-1,4-BENZOXAZINE

7-{2-[4-(4-FLUORO PHENYL)PIPERAZIN-1-YL]ETHYL}-2,3-DIHYDRO-3-OXO-1,4-BENZOXAZINE

7-{4-[4-(3-TRIFLUOROMETHYL)PIPERAZIN-1-YL]BUTYL}-2,3-DIHYDRO-3-OXO-1,4-BENZOXAZINE

7-{4-[4-(2-METHOXY PHENYL)PIPERAZIN-1-YL]BUTYL}-2,3-DIHYDRO-3-OXO-1,4-BENZOXAZINE

7-{4-[4-(4-FLUORO PHENYL)PIPERAZIN-1-YL]BUTYL}-2,3-DIHYDRO-3-OXO-1,4-BENZOXAZINE

7-{2-[4-PHENYL PIPERAZIN-1-YL]ETHYL}-2,3-DIHYDRO-3-OXO-1,4-BENZOXAZINE and its 4-methylated compound.

7-{4-[4-PHENYL PIPERAZIN-1-YL]BUTYL}-2,3-DIHYDRO-3-OXO-, 14-BENZOXAZINE and its 4-methylated compound.

PHARMACOLOGICAL STUDY OF THE COMPOUNDS OF THE INVENTION

EXAMPLE A: IN VITRO AFFINITY TEST FOR 5-HT$_{1A}$, 5-HT$_2$, D$_2$ and $\alpha_2$ RECEPTORS The in vitro affinity tests for 5-HT$_{1A}$, 5-HT$_2$, D$_2$ and $\alpha_2$ receptors were carried out according to conventional binding techniques.

The results of these studies show that the compounds of the invention possess a K0.5 of the order of $10^{-10}$M with respect to 5-HT$_{1A}$ receptors. This very great affinity is complemented by a very great selectivity. In effect, the ratio of the 5-HT$_{1A}$/D2 affinities is equal to 100. That of the 5-HT$_{1A}$/$\alpha$2 affinities is equal to 104 and that of 5-HT$_1$A/5-HT$_2$ affinities is close to 103.

EXAMPLE B: Acute Toxicity

The acute toxicity was assessed after oral administration of a dose of 650 mg.kg$^{-1}$ to batches of 8 mice (26±2 grams). The animals were observed at regular intervals during the first day and daily during the two weeks following the treatment.

It is apparent that most of the compounds of the invention are completely non-toxic. Most of them cause no deaths after administration at a dose of 650 mg.kg$^{-1}$, and no disorders are generally observed after administration of this dose.

EXAMPLE C: STUDY OF ANXIOLYTIC ACTIVITY - PIGEON CONFLICT TEST

Six White Carneaux pigeons not previously used in experiments are trained to peck a Plexiglass key which is transilluminated by red or white lights. The response key is mounted on the front wall of the experimental chamber. The pigeons are brought to 85% of their normal weight before the beginning of the experiment, which is carried out using the method of successive approximations (Frester 1953). At the start, each peck of the key (illuminated with a red or white light) which exceeds a force of 0.15N permits access to a mixture of cereals via an automatic dispenser located under the key. After several days, the cereals are no longer delivered until the thirtieth peck on the key. When this response to the 30th strike is obtained, and when it occurs regularly, permitting the delivery of feed, the color of the light of the key is alternated every three minutes (from white to red and vice-versa). The measurement of the level of response to the 30th strike remains operative during each light phase.

During this phase and throughout the experiment, a daily session is composed of 5 cycles of 3 minutes of each light sequence, these sequences being separated by a 30-second interval during which the luminous keys are extinguished and the responses have no effect. Consequently, a sequence lasts approximately 35 to 40 minutes. When these levels of responses are stable and identical for each color during a period of 5 days (this requires 3 to 4 weeks), every 30th response in one of the colored phases simultaneously brings about a release of feed and a brief (200-millisecond) and moderate (1.3 mA) electric shock delivered by electrodes placed on the pubic pones. The level of responses is reduced at first, then returns to the initial value.

The administration of the products of the invention is carried out after a stable level of response is obtained over a period of 5 days.

The intramuscular injection of the products of the invention at a dose of 0.3 mg/kg$^{-1}$ brings about a significant increase in response whether or not followed by electric shocks, demonstrating the anxiolytic activity of these products.

EXAMPLE D: STUDY OF HYPNOTIC ACTIVITY

Male IFFA-CREDO strain OF1 mice weighing on average 22±2 grams receive by esophageal intubation a solution consisting of gum arabic containing the test compound, namely 10 mg.kg$-1$, on the basis of 0.25 ml per 20 g of body weight. The time taken by the animal to fall asleep after being placed in dorsal decubitus and the duration of sleeping are noted. Pentobarbital is taken as a reference at a dose of 50 mg.kg$^{-1}$.

It is apparent that some compounds of the invention at a dose of 10 mg.kg$^{-1}$ have a hypnotic activity greater than that of pentobarbital at a dose of 50 mg.kg$-1$, taken as a reference.

EXAMPLE E: INTERACTION WITH THE EFFECTS OBTAINED IN RATS WITH APOMORPHIN

This test has been carried out in male SPRAGUE-DAWLEY rats having an average weigh of 140±10 grams.

The compounds of the invention are administered at various doses (16, 8,4, 2 or 1 mg.kg$^{-1}$).

Each dose is administered to a group of six animals.

The studied compounds are administered as a suspension in a mixture of gum syrup and purified water (50/50).

A group of six animals only received the mixture of gum syrup and purified water.

Thirty minutes after each treatment a solution of apomorphine in NaCl 0, 154M is administered by the subcutaneous route at a 1,5 mg.kg$-1$ dose.

Animals are put in plexiglass boxes which are in a room in which the temperature is maintained constant (22±1° C.). The numbering of the straightenings and stereotypies of animals is carried out during twenty minutes after the administration of apomorphine. A grading is used which permits to calculate the percentage of antagonism against apomorphine obtained by the studied compounds.

Thirty minutes after the administration of apomorphine the temperature is also measured.

It appeared that at 8 mg.kg$-1$ dose every compound of the invention having a phenyl piperazine moiety permits an antagonism of the apomorphine activities ranging from 90 to 100%. Some of them totally antagonizes the apomorphine activity at a 4 mg.kg$-1$ dose.

If we compare these results to those described in U.S. Pat. No. 3,770,734, it appeared that the preferred compound only permits when administered 30 minutes before apomorphine a 70% antagonism at 10 mg.kg$^{-1}$. An antagonism of 90% was obtained for only one compound at a 25 mg.kg$^{-1}$ dose. These results obtained with our compounds are consequently surprisingly better.

This improvement is confirmed when measuring hypothermia observed in treated animals. Every compound of our application having a phenyl piperazine moiety permits at a 2 mg.kg$-1$ dose the observation of a hypothermia ranging from 1,8° C. to 4° C. The preferred compound of U.S. Pat. No. 3,770,734 only permits the observation of an hypothermia of 1°5 after administration of a 5 mg.kg$^{-1}$ dose.

These tests reflect the depressive activity of the compounds of the invention on the central nervous system. It appears that the compounds of this invention have an activity which can be compared to that of the best compounds of U.S. Pat. No. 3,770,734 administered at doses ranging from 2 to 6 fold higher than the compounds of the present invention.

EXAMPLE E: PHARMACEUTICAL COMPOSITIONS

Tablets intended for the treatment of psychic disorders, containing 2,5 mg of 4-methyl-6-{4-(2-methoxyphenyl)-1-piperazinyl]butyl}2,3-dihydro 3-oxo- 1,4-benzoxazine hydrochloride.

| Preparation formula for 1,000 tablets | |
|---|---|
| 4-Methyl-6-{4-[4-(2-methoxyphenyl)-1-piperazinyl] ethyl} hydrochloride | 2 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

We claim:

1. A compound selected from those of formula (I):

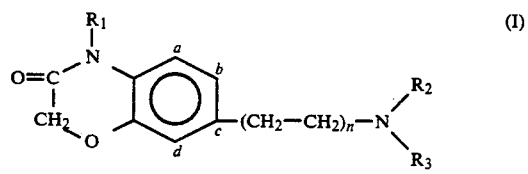

in which:
R$_1$ represents hydrogen or lower alkyl,
n represents 1 or 2,
R$_2$ and R$_3$, which may be identical or different, each represents, independently of one another:
hydrogen, lower alkyl, phenyl(lower alkyl), hydroxy phenyl (hydroxy lower alkyl), or phenyl, or R$_2$ and R$_3$, together with the nitrogen atom which carries them, form a 1-piperazine ring 4-substituted with a phenyl, phenyl(lower alkyl), pyridyl, or pyrimidinyl group, or with a phenyl group substituted with one or more lower alkyl, trifluoromethyl, lower alkoxy groups, or halogen atoms, or with a phenyl(lower alkyl) group substituted on the phenyl ring with one or more lower alkyl, trifluoromethyl, lower alkoxy groups, or halogen atoms,
their enantiomers, diastereoisomers and epimers as well as their addition salts with a pharmaceutically-acceptable acid or a pharmaceutically-acceptable base when R$_1$=H.

2. A compound selected from those claimed in claim 1 in which R$_2$ and R$_3$, with the nitrogen atom which carries them, form a piperazine which is substituted on the piperazine nitrogen numbered 4 with a phenyl or phenyl(lower alkyl) group, the phenyl and phenyl alkyl groups themselves being unsubstituted or substituted on the aromatic ring with one or more lower alkyl, trifluoromethyl, or lower alkoxy groups or halogen atoms, its enantiomers, epimers and diastereoisomers as well as its addition salts with a pharmaceutically-acceptable acid or a pharmaceutically-acceptable base when R$_1$=H.

3. A compound as claimed in claim 1 which is selected from 7-{2-[4-(3-trifluoromethylphenyl)-1-piperazinyl]ethyl}-2,3-dihydro-3-oxo-1,4-benzoxazine, its 4-methylated compound, and addition salts thereof with a pharmaceutically-acceptable acid or base.

4. A compound as claimed in claim 1 which is selected from 7-{2-[4-(2-methoxyphenyl)-1-piperazinyl]ethyl}-2,3-dihydro-3-oxo-1,4-benzoxazine, its 4-methylated compound, and addition salts thereof with a pharmaceutically-acceptable acid or base.

5. A compound as claimed in claim 1 which is selected from 7-{2-[4-(4-fluorophenyl)-1-piperazinyl]e- thyl}-2,3-dihydro-3-oxo-1,4-benzoxazine, its 4-methylated compound, and addition salts thereof with a pharmaceutically-acceptable acid or base.

6. A compound as claimed in claim 1 which is selected from 7-{4-[4-(3-trifluoromethylphenyl)-1-piperazinyl]butyl}-2,3-dihydro-3-oxo-1,4-benzoxazine, its 4-methylated compound, and addition salts thereof with a pharmaceutically-acceptable acid or base.

7. A compound as claimed in claim 1 which is selected from 7-{4-[4-(2-methoxyphenyl)-1-piperazinyl]-butyl}-2,3-dihydro-3-oxo-1,4-benzoxazine, its 3-methylated compound, and addition salts thereof with a pharmaceutically-acceptable acid or base.

8. A compound as claimed in claim 1 which is selected from 7-{4-[4-(4-fluorophenyl)-1-piperazinyl]-butyl}-2,3-dihydro-3-oxo 1,4-benzoxazine, its 4-methylated compound, and addition salts thereof with a pharmaceutically-acceptable acid or base.

9. A compound as claimed in claim 1 selected from those in which NR$_2$R$_3$ denotes a 1-(2-pyrimidyl)piperazine, as well as addition salts thereof with a pharmaceutically-acceptable acid or base.

10. A compound as claimed in claim 1 which is selected from 7-{4-[4-phenyl piperazin-1-yl]butyl}-2,3-dihydro-3-oxo-1,4-benzoxazine, its 4-methylated compound, and addition salts thereof with a pharmaceutically-acceptable acid or base.

11. A compound as claimed in claim 1 which is selected from 7-{2-[4-phenyl piperazin-1-yl]ethyl}2,3-dihydro-3-oxo 1,4-benzoxazine, its 4-methylated compound, and addition salts thereof with a pharmaceutically-acceptable acid or base.

12. A pharmaceutical composition containing as active principle at least one compound as claimed in claim 1, in combination with one or more pharmaceutically-acceptable, excipients or vehicles.

13. A method for treating a mammal afflicted with a serotoninergic system disorder requiring for its treatment a 5-HT1A agonist comprising the step of administering to the said mammal an amount of a compound of claim 1 which is effective for alleviation of said condition.

* * * * *

UNITED STATES PATENT AND TRADEMARK OFFICE
CERTIFICATE OF CORRECTION

PATENT NO. : 5,225,409
DATED : July 6, 1993
INVENTOR(S) : Thierry Taverne, Isabelle Lesieur, Patrick Depreux,
Daniel H. Caignard, Beátrice Guardiola, Gérard Adam,
Pierre Renard It is certified that error appears in the above-indentified patent and that said Letters Patent is hereby corrected as shown below:

Column 4, approximately line 36; "produce" should read
-- product --.
Column 6, line 4; "[2-}2-" should read -- [2-{2- --.
Column 6, approximately line 59; "-1-(PIPERAZINYL]"
should read -- -1-PIPERAZINYL] --.
Column 12, line 68; move the "e" at the end of line 68 to
the top of column 13, line 1, and insert before "thyl".

Signed and Sealed this

Twenty-sixth Day of April, 1994

Attest:

BRUCE LEHMAN

Attesting Officer

Commissioner of Patents and Trademarks